United States Patent [19]

Bichon et al.

[11] Patent Number: 4,987,181

[45] Date of Patent: Jan. 22, 1991

[54] SUBSTRATE WITH AN ANTITHROMBOGENIC ACTIVE SURFACE

[75] Inventors: Daniel Bichon, Gaillard; Christian Guillot, Saint Julien en Genevois, both of France; Michel Schneider, Troinex, Switzerland

[73] Assignee: Battelle Memorial Institute, Switzerland

[21] Appl. No.: 409,988

[22] Filed: Sep. 19, 1989

Related U.S. Application Data

[63] Continuation of Ser. No. 34,162, filed as PCT CH86/00093 on Jul. 3, 1986, published as WO87/00006 on Jan. 15, 1987, abandoned.

[30] Foreign Application Priority Data

Jul. 8, 1985 [CH] Switzerland ..................... 2954/85

[51] Int. Cl.$^5$ .................... A61K 17/00; A61K 19/00; A61K 29/00
[52] U.S. Cl. .................... 525/54.1; 523/112; 514/822; 604/96; 604/266; 427/2; 525/54.2
[58] Field of Search .............. 523/112; 525/54.1, 54.2; 514/822; 424/101; 604/96, 266; 427/2

[56] References Cited

U.S. PATENT DOCUMENTS

| | | | |
|---|---|---|---|
| 3,826,678 | 7/1974 | Hoffman et al. | 428/411.1 |
| 4,521,564 | 6/1985 | Solomon et al. | 525/54.1 |
| 4,526,714 | 7/1985 | Feijen et al. | 424/101 |
| 4,720,512 | 1/1988 | Hu et al. | 523/112 |

FOREIGN PATENT DOCUMENTS

0086186  8/1983  European Pat. Off. .
2187849  1/1974  France .

Primary Examiner—Nathan M. Nutter
Attorney, Agent, or Firm—Cushman, Darby & Cushman

[57] ABSTRACT

Copolymer film deposited on a substrate comprising covalently fixed fragments of heparin having antithrombogenic properties. The polymer further comprises free carboxylic groups intended to neutralize free amine functions which are possibly present and to improve the hemocompatibility of the film.

6 Claims, No Drawings

SUBSTRATE WITH AN ANTITHROMBOGENIC ACTIVE SURFACE

07/034,162, filed as PCT CH86/00093 on Jul. 3, 1986, published as WO87/0006 on Jan. 15, 1987 which was abandoned upon the filing hereof.

The present invention concerns a substrate with an antithrombogenic surface resulting from the presence of an adhesive film bound thereto, this film being made of a polyolefinic copolymer which comprises side-groups distributed randomly on the main chain; these side groups are carboxylic groups and groups of formula

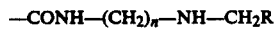
—CONH—(CH$_2$)$_n$—NH—CH$_2$R wherein R is heparin or an antithrombogenically active fragment derived from heparin by the depolymerization thereof, and n is an integer from 2 to 12.

The present copolymer may also comprise, as side groups, groups —CONH—(CH$_2$)$_n$—COOH in which n is from 1 to 12.

The copolymer film of the invention therefore has blood anticlotting properties and is particularly suited for coating substrates of various sorts, namely plastics used in blood transfusion devices.

The quantity of the free —COOH groups in the present polymer is stoichiometrically sufficient, and even in excess, to neutralize if necessary the basic conditions which result from the presence in the present copolymer of amine functions, and therefore improve the hemocompatibility of the surface coated with the antithrombogenic film (see for instance J. S. BYCK et al., Soc. Plast. Eng. Techn. Pap. 21, 563–566 (1975). Moreover, as a result from the manufacturing process disclosed hereafter, the present film is practically free from free primary amino groups, which imparts thereto an additional advantage over the anticlotting polymers of the prior art. This is so because in the basic process for making these polymers, a heparin depolymerization fragment is linked to a polymer comprising free amino-groups, this fragment includes a function reactive toward these free amino-groups, namely aldehyde groups, by a SCHIFF reaction followed by the reduction of the —N=C— bond resulting therefrom. Now, the formation of SCHIFF's bases is not quantitative and the antithrombogenic polymer which results from the above-mentioned process contains free —NH$_2$ functions which have a disturbing activity on the antithrombin activity of the bound heparin.

The following references provide details on films whose surface has anticlotting properties and which are known in the prior art: EP-A-86.187; EP-A-86.186; M. FUNASHI et al., Analytical Biochemistry 126, 414–421 (1982); P. OLSSON et al., Annals of the New York Academy of Sciences 1984, pp. 525–535; EP-A-98.814; EP-A-92.928. The following documents, uncovered during a search effected by the Vienna Patent Office, are particularly significant.

Document U.S. Pat. No. 3,673,612 (MIT) discloses polymer compositions containing heparin. In these compositions, heparin is linked to the polymer backbone by acetal or hemiacetal bonds.

Document U.S. Pat. No. 4,239,664 (RESEARCH CORP.) discloses a polymer of polyvinyl-pyrrolidone and heparin in which the bond between the polymer links and heparin is an imino group. This polymer has antithrombogenic properties and can be used for making prosthesis and medical devices which are in contact with the blood of patients.

Document EP-A-46.828 (TEIJIN) discloses the esterification of heparin with acrylic and methacrylic derivatives and the binding of the esterified heparin on polymeric surfaces, these surfaces being that of medical devices, e.g. catheters, transfusion pipes, dialysis membranes, pump components, etc. The binding is effected under irradiation by U.V., electron beams or γ-rays. This document further discloses the heparinization of plastics with a structure comprising acid halide or anhydride groups; the heparinization reaction also involves esterification.

Document JP-82 39.851 (TERUMO) discloses quaternization of poly-N,N-dimethylaminoethyl-methacrylate and the binding of heparin on this polymer.

Document JP-82 18.705 (GIJUTSUIN) discloses the preparation of an anti-clotting material by the reaction of acrylonitrile with glycidyl methacrylate and the binding of heparin on the obtained polymer. A polymer of this kind is, in principle, somewhat similar to that of the invention but its backbone is quite different and it does not have free carboxylic acid groups.

Moreover, in the case when the present copolymer further comprises —CONH—(CH$_2$)$_n$—COOH groups, the latter groups contribute to reduce the adsorption of fibrinogen because they adsorb the albumin of plasma, which effect further decreases the tendency, if any, of blood clotting in the presence of a wall coated with such a polymer. The anti-clotting film coated on the substrate of the invention provides therefore significant advantages over the corresponding known products. In the various articles which can incorporate the substrate of the invention, the followings are cited: catheters, flexible nylon tubing, polyethylene, polyester or polyurethane used for surgery, containers for storing blood, pumps and pump members and all other elements which can be introduced into the bloodstream of a patient or be contacted with the blood outside or inside the body of the patient.

In the various possible compositions of the copolymer which constitutes the adhesive film used in the invention, the following can be cited: photo-copolymers based on acrylic acid, dimethylamino-ethylmethacrylate (DMAEMA), dimethylacrylamide and a co-monomer capable of binding a heparin fragment, namely N-hydroxysuccinimide acrylate (ANHS). One advantage of such copolymers is that they strongly stick to most usual plastic surfaces and they can be obtained very easily and quickly by irradiation, in the presence of an initiator, of a film from an appropriate composition containing the corresponding monomers. In addition to the foregoing monomers, the present composition may also contain other acrylic monomers, namely alkyl acrylates like isopropyl-butyl-, amyl-acrylate and other acrylates, acrylamide and acrylic prepolymers of the kind recited in document U.S. Pat. No. 4,451,568; these products have a relatively high molecular weight and they influence the viscosity of the monomer mixture. Stoichiometrically, the amount of acrylic acid in the above composition exceeds that of the DMAEMA to ensure that the amount of —COOH groups always exceed that of the dimethylamino groups. Thus, for one mole of DMAEMA, 1.01 to 2 moles of acrylic acid are used.

The radical R defined as a heparin fragment is derived from heparin depolymerization products, for instance by deaminative splitting of heparin as disclosed by OLSSON (see the aforementioned reference).

For preparing the substrate according to the invention, a selected article is coated by usual means (brush, dipping, spray) with a thin layer of a photopolymerizable monomer mixture of the aforementioned kind together with an initiator and it is subjected to photopolymerization under irradiation by usual means; when the film has been cured to a sufficient extent, it is bound to the heparin derivative through a bridging diamine of the formula $H_2N-(CH_2)_n-NH_2$ so as to achieve a connecting link (defined in the foregoing section as the formula $-NH-(CH_2)_n-NH-$); this link makes it possible to bind the copolymer and the heparin fragment.

Preferably, this link is achieved by the reaction of this aliphatic diamine with a group —CHO bound to the heparin fragment as it comes from the fragmentation reaction of OLSSON (see the foregoing reference). According to this worker, the reaction of heparin with nitrous acid transforms the 2-amino-2-desoxy-D-glucopyranosyl residue into an aldehyde residue from 2,5-anhydro-D-mannose which exhibits anticlotting properties like the starting heparin. The above coupling reaction thus provides a SCHIFF base which is thereafter reduced (for instance with sodium cyanoboride) to obtain an $R-CH_2-NH-(CH_2)_n-NH_2$ substituent. The latter is then reacted with the dry polymer film which comprises, as indicated hereabove, a group copolymerized with the other monomers, this group being capable of being bound to the free amine function of the bridging arm attached to the heparin fragment. This group, e.g. the N-hydroxysuccinimide group (NHS), is very labile and reacts as follows:

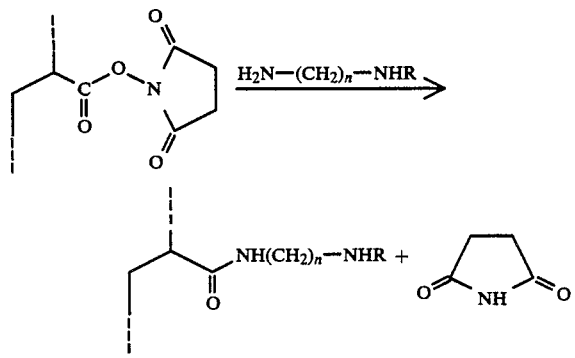

This operation therefore effects the binding of the heparin fragment R to the copolymer film by means of the foregoing connecting link. To prepare the latter, an advantageously used diamine is hexamethylene diamine, but of course, any other diamine included within the foregoing limits can be convenient, namely ethylene diamine, propylene diamine, butylene diamine, etc.

When the linking of the heparin group is accomplished, the remaining NHS functions are neutralized with an adequate reactant, for instance ethanolamine, glycine or other carboxyalkyl amines which step is advantageous in this case because it provides side chains with carboxy groups. It is also possible to proceed in the reverse direction to achieve the present antithrombogenic film, i.e. the diamine is bonded to the copolymer first and, afterwards, the aldehyde group of the heparin fragment is reacted with the aminated copolymer; this reaction is followed by a reduction with sodium borocyanide. In this case, the possible presence of free —NH2 groups (not having reacted with the aldehyde) has only a limited negative influence since there is an excess of —COOH groups.

As polymerization photoinitiators, benzophenone, its derivatives and other usual photoinitiators can be used, e.g. the photoinitiators disclosed in document EP-A-69.133.

The following examples illustrate the invention.

EXAMPLE 1

(a) Preparation of a substrate coated with a film having antithrombogenic properties PVC plates were selected with a titration recess or well (Microtiter plate FALCON) and coated with a film of a monomer mixture with the following ingredients:

| | |
|---|---|
| Dimethylacrylamide | 45 g |
| Acrylic acid | 15 g |
| DMAEMA | 25 g |
| ANHS | 10 g |
| P-36 | 5 g |
| Total | 100 g |

The product defined as P-36 is a photoinitiator of benzophenone structure provided by the U.C.B. Company (Belgium).

The plates were irradiated for 5 min under nitrogen by means of a UV lamp giving a flux of 30 W/cm at a distance of 30 cm, which provided on the walls of the wells a reactive film about 10–50 μm thick.

Furthermore, a sample of heparin was deaminated according to J. E. SHIVELY et al., Biochemistry 15 (18), 3392 (1976): to 0.1 g of heparin dissolved in 4.5 ml of aqueous citric acid (0.2M, pH 4) was added 0.5 ml of aqueous 1M sodium nitrite solution. After 30 min at room temperature, the pH was adjusted to 7 (0.1N NaOH solution) and the mixture was dialyzed in distilled water (SPECTRAPOR membrane, porosity cut-off at molecular weight 1000).

A quantity of hexamethylene diamine (HMD, 3M aqueous solution) sufficient to achieve a final concentration of 0.8M was added to the dialyzed solution of aldehyde heparin fragments (Hep-CHO). After incubating for 3 hrs at room temperature, the imine was reduced upon addition of 1 ml of a 1M solution of NaCNBH3 and, after 2 hrs, another dialysis was carried out in pure water, at 4° C., with a membrane identical to the aforementioned one. Finally, the dialyzed product (HMD-Hep) was contacted with Aquacid (sodium carboxymethylcellulose) until its volume was made to 3.5 ml. This solution was thereafter diluted to 28 mg/ml with 0.04M, pH 8 phosphate buffer.

Quantities of 200 μl of the HMD-hep solution were introduced into the wells coated with a reactive coating as described above and they were allowed to stand to incubate for 2 days. The wells were rinsed with distilled water after which quantities of 200 μl of aqueous 1M glycine solution were introduced therein for neutralizing the excess of untransformed hydroxysuccinimide groups into —COOH groups. Then rinsing with stirring was carried out, with water first, then with PBS (phosphate buffered saline: 0.15M NaCl, 10 mM Na2HPO4, pH 7.4). The cuvettes completed as described were labelled "Tests 1".

(b) Measurement of the thrombin blocking capacity

The measurement of the heparin antithrombin activity is based on its effect, in combination with antithrombin III, to block the activity of thrombin. For making the measurement, a known excess of thrombin is added to the test solution and the residual quantity of the thrombin is determined by its enzymatic activity.

The reagents used are derived from a kit of BOEHRINGER (Mannheim) for measuring small doses of heparin. The thrombin excess is measured by its catalytic action on the hydrolysis of a p-nitroanilide-polypeptide (CHROMOZYM-TH) which sets free p-nitroaniline which is titrated colorimetrically.

The "thrombin" reagent is prepared from the following ingredients: 10 ml of Tris HCl buffer (200 mM, pH 3.1), 25 mM NaCl; 6.5 IV/ml of aprotinine; 100 μl of thrombin solution (2.2 U/ml), 300 μl of antithrombin III solution SIGMA, (10 U/ml).

For making the measurement, 100 μl of the above reagent are added to the well to be tested and, after a given incubation time (for instance 3 min), a constant quantity of the CHROMOZYM-TH reagent is added and, after diluting to a given volume, the intensity of the color is measured at 405 nm, the latter being in proportion to the amount of non-inhibited thrombin. The results obtained (test 1) are given hereafter.

(c) Measure of the thrombin time

For this measurement, the reagents of the BOEHRINGER kit "Thrombin reagents" were used.

One hundred μl of platelet poor plasma (PPP) were added to one of the "heparinized" wells disclosed heretofore and the liquid was stirred gently for 2 min at 37° C. with a magnetic stirrer. Then, 100 μl of the "thrombin reagent" were added and the time needed for a white coagulum (fibrin) to form was measured. The results are gathered in the table hereafter in example 2.

EXAMPLE 2

Plates provided with titration cuvettes (wells) were selected and coated with cured photopolymer as disclosed at the beginning of paragraph (a) of example 1. These cuvettes were treated overnight with a 1M solution of HMD (Test 2). In addition, in order to have a control prepared according to the prior art, a cuvette was treated with a 10% by weight solution of polyethylene-imine (sample labelled ii). A control with no activation (iii) was also prepared by simply neutralizing the NHS reactive groups on the film with ethanolamine.

Thereafter, the solution which resulted from deamination of heparin as disclosed above was used for the trials (cuvettes Test 2, ii and iii); this solution was taken after dialysis but before the addition of HMD, it was diluted beforehand to about 5 mg/l in 0.1M phosphate buffer, pH 8. Two hundred μl of this solution were introduced into each sample and, after incubating overnight at room temperature, an excess of a 1M solution of sodium borocyanide solution was added to reduce the —N=C bond, then rinsing successively with water, PBS and serum. Regarding control (iii), since the film no longer had binding sites, it is assumed that the heparin fragments which were not bound had been eliminated by rinsing.

Samples labelled Test 2, ii and iii were tested, as well as the sample of example 1 (Test 1); the results are gathered in the table below.

| Sample | Antithrombin activity (U) | Thrombin time (sec) |
| --- | --- | --- |
| Test 1 | 0.12 | >300 |
| Test 2 | 0.10 | >300 |
| ii | 0.01 | 22 |
| iii | 0.03 | 28 |

These results show that the substrate of the invention (Test 1 and 2) has an antithrombin activity greatly exceeding that of a sample (ii) prepared according to the prior art. Furthermore, it is noted that the residual amino-groups of sample (ii) have an inhibitor effect (c.f. with the inactivated control iii) on the antithrombin activity of bound heparin.

We claim:

1. Substrate having on at least a portion of its surface an adhesive film with antithrombogenic properties, characterized in that this film is constituted of an olefinic copolymer comprising, covalently bound to the main chain and distibuted rendomly thereon, free carboxylic side groups and groups of formula —CONH—(CH$_2$)$_n$—NH—CH$_2$R (I) wherein R is a heparin molecule or a depolymerization fragment thereof and n is a integer from 2 to 12.

2. Substrate according to claim 1, characterized in that the copolymer comprises segments derived from the following monomers: acrylic acid, N,N-dimethylaminoethyl methacrylate, dimethylacrylamide, and amido-acrylic derivatives in which the amide group is that represented by formula I.

3. Substrate according to claim 1, further characterized by side groups of formula —CONH—(CH$_2$)$_n$—COOH wherein n is from 1 to 12.

4. Substrate according to claim 1, characterized in that R is a fragment issued from the HNO$_2$ deamination of heparin.

5. A substrate according to claim 1 in the form of a component of a surgical device for contact with blood.

6. A substrate according to claim 5 suitable for use in a surgical device selected from catheters, flexible tubings, containers or pumps.

* * * * *